United States Patent [19]

Riebel et al.

[11] 4,350,824
[45] Sep. 21, 1982

[54] PROCESS FOR THE PREPARATION OF 1,1-DICHLORO-ALKENES

[75] Inventors: Hans-Jochem Riebel; Fritz Maurer, both of Wuppertal; Uwe Priesnitz, Solingen, all of Fed. Rep. of Germany

[73] Assignee: Bayer Aktiengesellschaft, Leverkusen, Fed. Rep. of Germany

[21] Appl. No.: 236,484

[22] Filed: Feb. 23, 1981

[30] Foreign Application Priority Data

Mar. 12, 1980 [DE] Fed. Rep. of Germany ....... 3009486

[51] Int. Cl.³ .................... C07C 21/20; C07C 67/307
[52] U.S. Cl. .................... 560/124; 260/464; 260/465 D; 260/465 G; 560/21; 560/57; 560/101; 549/448; 549/451; 549/452; 549/454; 549/455; 562/435; 562/468; 562/491; 562/506; 564/166; 564/171; 564/181; 564/190; 568/348; 568/640; 568/655; 568/928; 568/933; 568/936; 570/184; 570/185; 570/189; 570/200; 570/217
[58] Field of Search .................. 560/124, 21, 57, 101; 570/183, 184, 185, 182, 186, 188, 193, 200, 237, 189, 217; 568/348, 655, 937, 936, 640, 928, 933; 260/464, 465 D, 465 G, 340.5 R; 562/506, 435, 468, 491; 564/190, 166, 171, 181

[56] References Cited

FOREIGN PATENT DOCUMENTS 2849 7/1979 European Pat. Off. ............ 560/124
48001 1/1980 European Pat. Off. ............ 560/124

*Primary Examiner*—Michael L. Shippen
*Attorney, Agent, or Firm*—Sprung, Horn, Kramer & Woods

[57] ABSTRACT

A process for the preparation of a 1,1-dichloroalkene of the formula

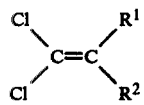

in which
$R^1$ is hydrogen, or an optionally substituted alkyl, alkenyl, alkinyl, cycloalkyl, aralkyl, aralkenyl or aryl radical, and
$R^2$ is an optionally substituted alkyl, alkenyl, alkinyl, cycloalkyl, aralkyl, aralkenyl or aryl radical, or
$R^1$ and $R^2$ together form an optionally branched and/or optionally benzo-fused hydrocarbon chain, comprising reacting a carbonyl compound of the formula

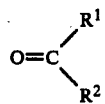

with a trichloromethanephosphonic acid ester of the formula

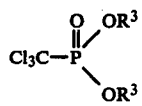

in which
$R^3$ each individually is an alkyl or phenyl radical, or the two radicals $R^3$ together are alkanediyl, in the presence of at least an equimolar amount of a phosphorous acid triamide of the formula

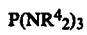

in which
$R^4$ each independently is an alkyl radical, or the two radicals $R^4$ together are alkanediyl.

Advantageously,
$R^1$ is hydrogen,
$R^2$ a $C_2$ to $C_5$ alkenyl radical, or a radical of the formula

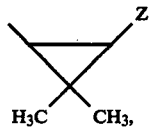

Z is a cyano, acetyl, carboxyl or $C_1$ to $C_4$ alkoxycarbonyl radical, or a radical of the formula —COOM,
M is sodium or potassium, and
$R^3$ each individually is a $C_1$ to $C_4$ alkyl or phenyl radical,
or the two radicals $R^3$ together are $C_2$ to $C_5$ alkandiyl, the phosphorous acid triamide is phosphorous acid tris-dimethylamide or tris-diethylamide, about 0.94 to 1.1 moles of each of trichloromethanephosphonic acid ester and of the phosphorous acid triamide are employed per mole of the carbonyl compound, and the reaction is effected at about 10° to 100° C. in a polar aprotic solvent.

10 Claims, No Drawings

PROCESS FOR THE PREPARATION OF 1,1-DICHLORO-ALKENES

The invention relates to an unobvious process for the preparation of certain 1,1-dichloroalkenes.

It is known that 1,1-dichloro-alkenes are obtained when lithium salts of dichloromethanephosphonic acid esters are reacted with aldehydes or ketones (see Synthesis 1975, 458–461 and 535–536). The preparation of the lithium salts of dichloromethanephosphonic acid esters is, however, troublesome. They are obtained from chloromethanephosphonic acid ester or trichloromethanephosphonic acid esters by reaction with butyl-lithium and, if appropriate, carbon tetrachloride at $-70°$ to $80°$ C., it being necessary to use carefully dried solvents and an inert gas atmosphere being required.

The present invention now provides a process for the preparation of 1,1-dichloro-alkenes of the general formula

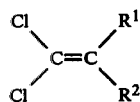

in which
R$^1$ represents a hydrogen atom or an optionally substituted alkyl, alkenyl, alkinyl, cycloalkyl, aralkyl, aralkenyl or aryl radical and R$^2$ represents an optionally substituted alkyl, alkenyl, alkinyl, cycloalkyl, aralkyl, aralkenyl or aryl radical,
or in which
the two radicals R$^1$ and R$^2$ together represent an optionally branched and/or optionally benzofused hydrocarbon chain,
in which a carbonyl compound of the general formula

in which
R$^1$ and R$^2$ have the abovementioned meaning,
is reacted with a trichloromethanephosphonic acid ester of the general formula

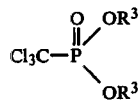

in which
the two radicals R$^3$ individually represent an alkyl or phenyl radical, or the two radicals R$^3$ together represent alkanediyl (alkylene),
in the presence of at least the equimolar amount of a phosphorous acid triamide of the general formula $$P(NR^4{}_2)_3 \quad (IV)$$

in which
R$^4$ represents alkyl radicals or the two radicals R$^4$ together represent alkanediyl (alkylene), optionally in the presence of a diluent and advantageously at a temperature between about 0° and 150° C.

It is surprising that 1,1-dichloro-alkenes of the formula (I) are obtained in good yields in a considerably simpler and less expensive manner by the process according to the invention than could be expected in view of the state of the art.

If, for example, 3-formyl-2,2-dimethyl-cyclopropane-1-carboxylic acid methyl ester, trichloromethanephosphonic acid dimethyl ester and phosphorous acid tris-dimethylamide are used as starting substances, the reaction according to the present invention is illustrated by the following equation:

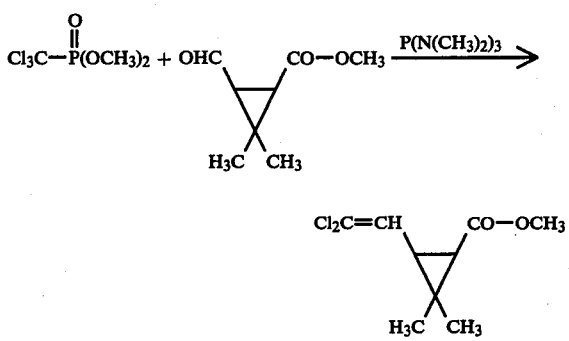

Preferred carbonyl compounds to be used as starting substances are those of formula (II) in which R$^1$ represents a hydrogen atom, an optionally halogen-substituted C$_1$ to C$_5$ alkyl radical, an optionally halogen-substituted benzyl or phenylethyl radical or a phenyl radical which is optionally substituted by halogen, C$_1$ to C$_4$ alkyl, C$_1$ to C$_4$ alkoxy, methylenedioxy, cyano and/or nitro, and R$^2$ represents an optionally halogen-substituted C$_1$ to C$_5$ alkyl radical, a C$_2$ to C$_5$ alkenyl or C$_2$ to C$_5$ alkinyl radical, an optionally halogen-substituted benzyl or phenylethyl radical, a phenyl radical which is optionally substituted by halogen, C$_1$ to C$_4$ alkyl, C$_1$ to C$_4$ alkoxy, methylenedioxy, cyano and/or nitro, an optionally halogen-substituted styryl radical or a radical of the general formula

wherein Z represents an acetyl, cyano, carbamoyl or C$_1$ to C$_4$ alkoxycarbonyl radical or a radical of the general formula COOM,
wherein M represents a hydrogen atom, an alkali metal, one alkaline earth metal equivalent or an ammonium radical.

Particularly preferred starting substances are those compounds of the formula (II) in which
R$^1$ represents a hydrogen atom and
R$^2$ represents a C$_2$ to C$_5$ alkenyl radical or
a radical of the general formula

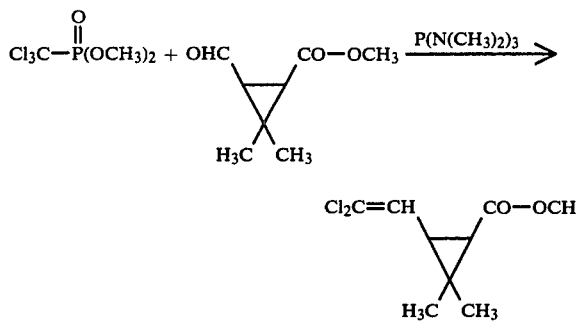

wherein
Z represents a cyano, acetyl, carboxyl or $C_1$ to $C_4$ alkoxycarbonyl radical or a radical of the general formula COOM,
wherein
M represents sodium or potassium.

Examples of the starting compounds of the formula (II) which may be mentioned are: $\beta,\beta$-dimethylacrolein, 3-formyl-2,2-dimethyl-1-cyano-cyclopropane, 3-formyl-2,2-dimethyl-1-acetyl-cyclopropane, 3-formyl-2,2-dimethyl-cyclopropane-1-carboxylic acid and its sodium salt, and 3-formyl-2,2-dimethyl-cyclopropane-1-carboxylic acid methyl ester, ethyl ester, n-propyl ester, iso-propyl ester, n-butyl ester, iso-butyl ester, sec.-butyl ester and tert. -butyl ester.

Compounds of the formula (II) are known (see Synthesis 1975, 535–536; and Tetrahedron Lett. 1976, 1,979–1,982). One synthesis is outlined by the following equation (in which R represent a $C_1$ to $C_4$ alkyl radical):

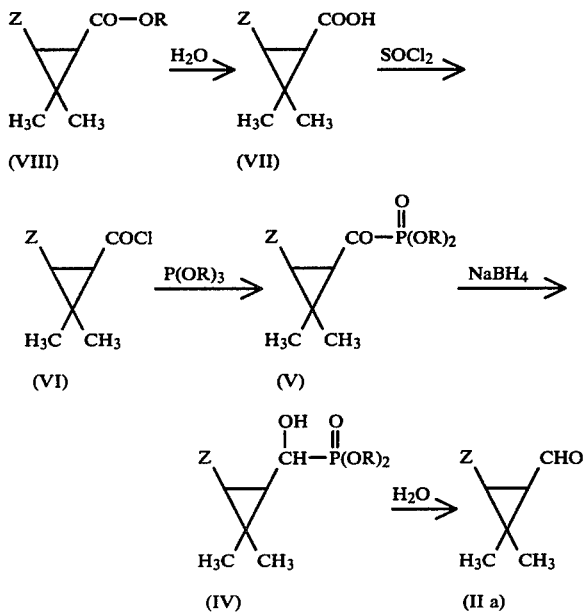

Hydrolysis of known cyclopropanecarboxylic acid esters of the formula (VIII) (see J. Org. Chem. 32 (1967), 3,351–3,355; Bull. Soc. Chim. Belg. 87 (1978), 721–732; and Tetrahedron Lett. 1978, 1,847–1,850), for example by reaction with aqueous-alcoholic potassium hydroxide solution at temperatures between 20° and 100° C. and subsequent acidification, gives the carboxylic acids of the formula (VII). These can be converted into the acid chlorides of the formula (VI) by reaction with halogenating agents, for example thionyl chloride, at temperatures between 20° and 80° C.

Reaction of the acid chlorides (VI) with trialkyl phosphites at temperatures between −20° and +150° C., preferably between 0° and 120° C., gives the cyclopropanoylphosphonic acid esters of the formula (V) (see J. Am. Chem. Soc. 86 (1964), 3,862–3,866; and Methoden der organischen Chemie (Methods of Organic Chemistry) (Houben-Weyl-Müller), 4th edition, volume 12/1, page 453, Georg-Thieme-Verlag, Stuttgart 1963). The products are isolated and purified, if appropriate, by distillation under reduced pressure.

The $\alpha$-hydroxy-phosphonic acid esters of the formula (IV) are obtained by reducing the oxo compounds of the formula (V) with sodium tetrahydridoborate, if appropriate using a diluent, for example water or aqueous methanol, at temperatures between −20° and +50° C., the pH value being kept between 5 and 8 by adding a buffer agent, for example sodium hydrogen phosphate (see Chem. Ber. 103 (1970), 2,984–2,986). For working up, the mixture is extracted with a water-immiscible solvent, for example methylene chloride, the extracts are dried and filtered and the solvent is distilled off from the filtrate under reduced pressure.

The corresponding aldehydes of the formula (IIa) can be prepared from the $\alpha$-hydroxy-phosphonic acid esters of the formula (IV) by treatment with sodium hydroxide solution at temperatures between 0° and 100° C., preferably between 10° and 50° C. (see Chem. Ber. 103 (1970), 2,984–2,986).

As an alternative to the preparation process outlined above, aldehydes of the formula (IIa) are also obtained by reacting acid chlorides of the formula (VI) with lithium tri-tert.-butoxy-hydrido-aluminate, which has been prepared, if appropriate, in situ from lithiumtetrahydridoaluminate and tert.-butanol, the reaction being carried out, if appropriate, in the presence of a diluent, for example tetrahydrofurane, at temperatures between −100° and +100° C., preferably between −80° and +50° C. For working up, the mixture is poured into a mixture of hydrochloric acid and icewater and is extracted with a water-immiscible solvent, for example diethyl ether. The extracts are dried, filtered and concentrated. The crude product is purified, if appropriate, by distillation.

Preferred trichloromethanephosphonic acid esters of formula (III) also to be used as starting substances are those in which
the radicals $R^3$ individually represent a $C_1$ to $C_4$ alkyl or phenyl radical or the two radicals $R^3$ together represent $C_2$ to $C_5$ alkanediyl.

Examples which may be mentioned are trichloromethanephosphonic acid dimethyl ester, diethyl ester, dipropyl ester and diphenyl ester.

Compounds of the formula (III) are known (see J. Am. Chem. Soc. 69 (1947), 1,022; and ibid. 77 (1955), 1,156).

Preferred phosphorous acid triamides of formula (IV) also to be employed in the process according to the invention are those in which
$R^4$ represents $C_1$ to $C_4$ alkyl radicals or the two radicals $R^4$ together represent $C_2$ to $C_5$ alkanediyl.

Examples which may be mentioned are phosphorous acid tris-dimethylamide and tris-diethylamide.

If appropriate, the process according to the invention is carried out using diluents. Possible diluents are virtually any of the inert organic solvents, in particular aprotic polar solvents. These include ethers (for example glycol dimethyl ether, diglycol dimethyl ether, tetrahydrofuran and dioxane), carboxylic acid amides (for example dimethylformamide, dimethylacetamide and N-methyl-pyrrolidone), sulphoxides (for example dimethylsulphoxide), phosphoric acid amides (for example hexamethylphosphoric acid triamide), and nitriles (for example acetonitrile and propionitrile).

The reaction temperature can be varied within a substantial range. In general, the reaction is carried out between 0° and 150° C., preferably at 10° to 100° C.

The process according to the invention is in general carried out under normal pressure.

0.9 to 1.2 moles, preferably 0.95 to 1.1 moles, of each of the trichloromethanephosphonic acid ester of the formula (III) and of the phosphorous acid triamide of the formula (IV) are generally employed per mole of carbonyl compound of the formula (II).

For carrying out the process according to the invention, the starting substances of the formula (II) and (III) are preferably initially introduced into the reaction vessel and the phosphorous acid triamde is added dropwise. The reaction mixture is stirred until the reaction has ended and is then filtered.

Working up can be carried out by customary methods, for example by a procedure in which the filtrate is diluted with water and extracted with an organic solvent which is virtually immiscible with water, for example, methylene chloride, the organic phase is dried and filtered and the filtrate is evaporated. The products, which remain in the residue, can be purified in the customary manner, for example by vacuum distillation.

Some of the 1,1-dichloro-alkenes which can be prepared by the process according to the invention can be used as intermediate products for the preparation of insecticidally and acaricidally active pyrethroids (see DE-OS (German Published Specification) 2,326,077).

PREPARATIVE EXAMPLES

EXAMPLE 1

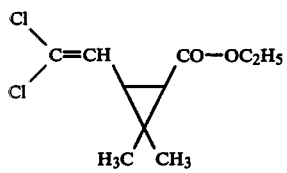

16.3 g (0.1 mole) of tris-dimethylaminophosphine were added dropwise to a mixture of 25.5 g (0.1 mole) of trichloromethanephosphonic acid diethyl ester and 17.2 g (0.1 mole) of 3-formyl-2,2-dimethyl-cyclopropane-1-carboxylic acid ethyl ester at a temperature of 40° C. The reaction mixture was then warmed to 90° C. for 3 to 4 hours. It was subsequently cooled and poured into 200 ml of water. This suspension was extracted twice with 100 ml of methylene chloride each time. The combined extracts were dried over sodium sulphate and then concentrated. 3-(2,2-Dichloro-vinyl)-2,2-dimethyl-cyclopropane-1-carboxylic acid ethyl ester was obtained in a yield of 88% of theory.

EXAMPLE 2

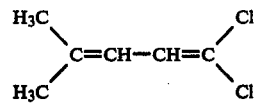

8.2 g (0.05 mole) of tris-dimethylaminophosphine were added to a mixture of 12.8 g (0.05 mole) of trichloromethane-phosphonic acid diethylester and 4.2 g (0.05 mole) of β,β-dimethylacrolein. The temperature thereby rose to about 35° C. The reaction mixture was subsequently stirred at room temperature for 3 hours and the reaction product was then distilled off. 1,1-Dichloro3,3-dimethylbutadiene of boiling point 50°–55° C./10 mm Hg was obtained in this manner.

It will be appreciated that the instant specification and examples are set forth by way of illustration and not limitation, and that various modifications and changes may be made without departing from the spirit and scope of the present invention.

We claim:

1. A process for the preparation of a 1,1-dichloroalkene of the formula

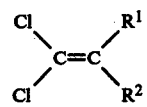

in which
R[1] is hydrogen, or an alkyl, alkenyl, alkinyl, cycloalkyl, aralkyl, aralkenyl or aryl radical, and
R[2] is an alkyl, alkenyl, alkinyl, cycloalkyl, aralkyl, aralkenyl or aryl radical, or
R[1] and R[2] together form an optionally branched and/or optionally benzo-fused hydrocarbon chain, comprising reacting a carbonyl compound of the formula

with a trichloromethanephosphonic acid ester of the formula

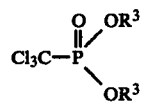

in which
R[3] each individually is an alkyl or phenyl radical, or the two radicals R[3] together are alkanediyl,
in the presence of at least an equimolar amount of a phosphorous acid triamide of the formula

in which
R[4] each independently is an alkyl radical, or the two radicals R[4] together are alkanediyl.

2. A process for the preparation of a 1,1-dichloroalkene of the formula

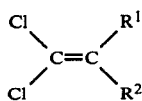

in which
R$^1$ is hydrogen, an optionally halogen-substituted C$_1$ to C$_5$ alkyl, benzyl or phenylethyl radical, or a phenyl radical which is optionally substituted by halogen, C$_1$ to C$_4$ alkyl, C$_1$ to C$_4$ alkoxy, methylenedioxy, cyano and/or nitro, and R$^2$ is an optionally halogen-substituted C$_1$ to C$_5$ alkyl, benzyl, phenylethyl or styryl radical, a C$_2$ to C$_5$ alkenyl or C$_2$ to C$_5$ alkinyl radical, a phenyl radical which is optionally substituted by halogen, C$_1$ to C$_4$ alkyl, C$_1$ to C$_4$ alkoxy, methylenedioxy, cyano and/or nitro, or a radical of the formula

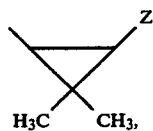

Z is cyano, carbamoyl or C$_1$ to C$_4$ alkoxycarbonyl radical, or a radical of the formula —COOM, and
M is hydrogen, an alkali metal, one alkaline earth metal equivalent or an ammonium radical,
comprising reacting a carbonyl compound of the formula

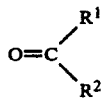

with a trichloromethanephosphonic acid ester of the formula

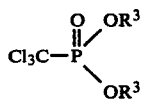

in which
R$^3$ each individually is an alkyl or phenyl radical, or the two radicals R$^3$ together are alkanediyl,
in the presence of at least an equimolar amount of a phosphorous acid triamide of the formula

in which
R$^4$ each independently is an alkyl radical, or the two radicals R$^4$ together are alkanediyl.

3. A process for the preparation of a 1,1-dichloroalkene of the formula

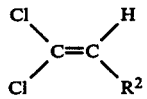

in which
R$^2$ is a C$_2$ to C$_5$ alkenyl radical, or a radical of the formula

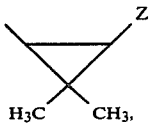

Z is a cyano, acetyl, carboxyl or C$_1$ to C$_4$ alkoxycarbonyl radical, or a radical of the formula —COOM, and
M is sodium or potassium,
comprising reacting an aldehyde of the formula

with a trichloromethanephosphonic acid ester of the formula

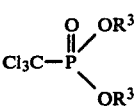

in which
R$^3$ each individually is an alkyl or phenyl radical, or the two radicals R$^3$ together are alkanediyl,
in the presence of at least an equimolar amount of a phosphorous acid triamide of the formula

in which
R$^4$ each independently is an alkyl radical, or the two radicals R$^4$ together are alkanediyl.

4. A process according to claim 1, 2 or 3, in which R$^3$ each individually is a C$_1$ to C$_4$ alkyl or phenyl radical, or the two radicals R$^3$ together are C$_2$ to C$_5$ alkandiyl.

5. A process according to claim 1, 2 or 3, in which R$^4$ each independently is a C$_1$ to C$_4$ alkyl radical, or the two radicals R$^4$ together are C$_2$ to C$_5$ alkanediyl.

6. A process according to claim 1, 2 or 3, in which the phosphorous acid triamide is phosphorous acid tris-dimethylamide or tris-diethylamide.

7. A process according to claim 1, in which the reaction is carried out at a temperature between about 0° and 150° C.

8. A process according to claim 1, in which the reaction is carried out in an inert organic solvent.

9. A process according to claim 1, in which about 0.95 to 1.9 mols of each of trichloromethanephosphonic acid ester and of the phosphorous acid triamide are employed per mol of the carbonyl compound.

10. A process according to claim 3, in which R$^3$ each individually is a C$_1$ to C$_4$ alkyl or phenyl radical, or the two radicals R$^3$ together are C$_2$ to C$_5$ alkandiyl, the phosphorous acid triamide is phosphorous acid tris-dimethylamide or tris-diethylamide, about 0.94 to 1.1 moles of each of trichloromethanephosphonic acid ester and of the phosphorous acid triamide are employed per mole of the carbonyl compound, and the reaction is effected to about 10° to 100° C. in a polar aprotic solvent.

* * * * *

UNITED STATES PATENT AND TRADEMARK OFFICE
CERTIFICATE OF CORRECTION

PATENT NO. : 4,350,824
DATED : September 21, 1982
INVENTOR(S) : Hans-Jochem Riebel et al It is certified that error appears in the above—identified patent and that said Letters Patent is hereby corrected as shown below:

Col. 3, lines 1-15     Delete formula and insert --

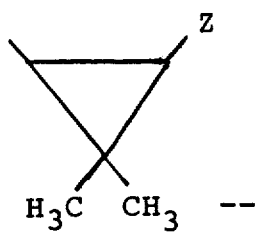

--

Signed and Sealed this

Fifteenth Day of February 1983

[SEAL]

Attest:

GERALD J. MOSSINGHOFF

Attesting Officer    Commissioner of Patents and Trademarks